United States Patent [19]

Jenck

[11] 4,454,333

[45] Jun. 12, 1984

[54] PALLADIUM CATALYZED CARBONYLATION OF CONJUGATED DIENES WITH CATALYST RECYCLE

[75] Inventor: Jean Jenck, Villeurbanne, France

[73] Assignee: Rhone-Poulenc Chimie de Base, Courbevoie, France

[21] Appl. No.: 401,338

[22] Filed: Jul. 23, 1982

[30] Foreign Application Priority Data

Sep. 16, 1981 [FR] France .............................. 81 17464

[51] Int. Cl.$^3$ .............................................. C07C 67/38
[52] U.S. Cl. ...................................... 560/1; 502/152; 502/171; 502/185; 252/472; 560/104; 560/114; 560/128; 560/192; 560/204; 560/207; 502/339
[58] Field of Search .................... 560/1, 104, 114, 128, 560/204, 207, 192; 252/437, 438, 431 R, 472; 546/248

[56] References Cited

U.S. PATENT DOCUMENTS

| | | | |
|---|---|---|---|
| 3,397,226 | 8/1968 | Fenton et al. | 560/204 X |
| 3,437,676 | 4/1969 | Kutepow et al. | 560/204 X |
| 3,530,168 | 9/1970 | Biale | 560/204 X |
| 3,952,034 | 4/1976 | Thompson et al. | 560/204 X |
| 4,259,519 | 3/1981 | Stille | 560/204 X |
| 4,259,520 | 3/1981 | Kummer et al. | 560/204 |
| 4,281,173 | 7/1981 | Kesling | 560/204 |

*Primary Examiner*—Natalie Trousof
*Assistant Examiner*—Vera C. Clarke
*Attorney, Agent, or Firm*—Burns, Doane, Swecker & Mathis

[57] ABSTRACT

Esters of $\beta,\gamma$-unsaturated carboxylic acids are prepared by (i) carbonylating a conjugated diene with carbon monoxide in the presence of an alcohol, a halogenated hydracid and a palladium catalyst; (ii) distilling the carbonylation reaction product in the presence of an ammonium, phosphonium or arsonium quaternary onium chloride or bromide having a melting point below the temperature at which the carbonylation reaction is carried out, and at a temperature and pressure such that said reaction product separates into a gaseous phase and a homogeneous liquid phase; (iii) recovering said gaseous phase comprising the ester of the $\beta,\gamma$-unsaturated carboxylic acid corresponding to the reactant diene and alcohol, any unreacted diene and alcohol, and any volatile reaction products of low molecular weight; (iv) recovering said homogeneous liquid phase comprising a mixture of the quaternary onium chloride or bromide and the palladium catalyst, and any nonvolatile reaction products of high molecular weight; and (v) recycling, advantageously after removing any reaction products of high molecular weight, the homogeneous liquid phase comprising said mixture of quaternary onium chloride or bromide and the palladium catalyst, into the carbonylation reaction medium.

25 Claims, No Drawings

PALLADIUM CATALYZED CARBONYLATION OF CONJUGATED DIENES WITH CATALYST RECYCLE

CROSS-REFERENCE TO RELATED APPLICATION

My copending application, Ser. No. 401,394, filed concurrently herewith, and assigned to the assignee hereof.

BACKGROUND OF THE INVENTION

1. Field of the Invention

The present invention relates to the preparation of esters of $\beta,\gamma$-unsaturated carboxylic acids by the carbonylation of conjugated dienes with carbon monoxide, in the presence of an alcohol, a halogenated hydracid and a palladium catalyst, with recovery and recycling of the said catalyst.

2. Description of the Prior Art

It is known to this art, from Japanese Patent No. 48.5564, to prepare monoesters of $\beta,\gamma$-unsaturated carboxylic acids by the carbonylation of conjugated dienes with carbon monoxide, in the presence of a monoalcohol, a non-halogenated palladium catalyst and a halogenated hydracid, at a temperature on the order of 100° C. and under a carbon monoxide pressure on the order of 100 bars; the patent is silent regarding any method for recovering the catalyst.

It has also been shown, per French Patent Application No. 81/01,205, filed Jan. 23, 1981, and assigned to the assignee hereof, that the selectivity in respect of the desired esters, the degree of conversion of the conjugated dienes employed and the stability of the palladium catalyst are improved if the medium subjected to carbonylation also contains a quaternary onium salt of an element of Group VB of the Periodic Table selected from among nitrogen, phosphorus and arsenic, and comprising an anion selected from among "hard" or "intermediate" bases [according to the definition set forth by R. Pearson in *J. Chem. Ed.*, 45, 581–7 (1968)].

Also, the said application does not indicate how to recover the palladium catalyst for the purpose of recycling it.

SUMMARY OF THE INVENTION

Accordingly, a major object of the present invention is the provision of an improved process for the preparation of esters of $\beta,\gamma$-unsaturated carboxylic acids by the carbonylation of conjugated dienes, which process can be carried out either continuously or batchwise.

Briefly, the present invention features a process for the preparation of esters of $\beta,\gamma$-unsaturated carboxylic acids by the carbonylation of conjugated dienes with carbon monoxide, in the presence of an alcohol, a halogenated hydracid and a palladium catalyst, such process comprising:

(i) distilling the carbonylation reaction product in the presence of a quaternary onium chloride or bromide selected from among quaternary ammonium, phosphonium and arsonium chlorides or bromides having a melting point below the temperature at which the carbonylation is carried out, under conditions of temperature and pressure such as to enable;

(ii) recovering a gas phase (iia) containing the ester of the $\beta,\gamma$-unsaturated carboxylic acid corresponding to the diene and the alcohol employed, the unreacted diene and alcohol and also the volatile products of low molecular weight; and (iib) a homogeneous liquid phase comprising a mixture of the quaternary onium chloride or bromide and the palladium catalyst, and also the non-volatile reaction products of high molecular weight; and (iii) recycling, after removal of the reaction products of high molecular weight, if appropriate, the said mixture of quaternary onium chloride or bromide and palladium catalyst, in the form of a homogeneous liquid, into the reaction medium subjected to carbonylation.

DETAILED DESCRIPTION OF THE INVENTION

More particularly according to this invention, the subject carbonylation of the conjugated dienes in the presence of a palladium catalyst is generally carried out at a temperature ranging from about 50° to 160° C., preferably from 80° to 150° C., the carbon monoxide pressure preferably ranging from about 50 to 250 bars.

The following are exemplary of the quaternary onium chlorides or bromides which can be present during the distillation operation: tetrabutylphosphonium chloride, melting at about 65° C.; methyl-tri-(octyl, nonyl or decyl)-ammonium chlorides or mixtures thereof marketed under the trademark Aliquat 336 or Adogen 464 and melting at about 100° C.; methyltributylammonium chloride, melting at about 102° C.; benzylbutyldimethylammonium chloride, melting at about 62° C.; benzylhexadecyldimethylammonium chloride, melting at about 60° C.; benzyldimethyltetradecylammonium chloride, melting at about 62° C.; hexadecyltributylphosphonium bromide, melting at about 57° C.; tetrabutylammonium bromide, melting at about 102° C.; tetradodecylammonium bromide, melting at about 91° C.; tetraheptylammonium bromide, melting at about 87° C.; tetrahexylammonium bromide, melting at about 90° C.; tetradecylammonium bromide, melting at about 88° C.; tetraoctadecylammonium bromide, melting at about 103° C.; tetraoctylammonium bromide, melting at about 94° C.; tetrapentylammonium bromide, melting at about 100° C.; tributylheptylammonium bromide, melting at about 58° C.; and tributylpentylammonium bromide, melting at about 64° C.

The amount of quaternary onium chloride or bromide which can be present during the distillation operation can vary over very wide limits, the minimum amount corresponding to a molar ratio quaternary onium cation/palladium of about 2. It is economically advantageous to use an amount of quaternary onium chloride or bromide corresponding to a molar ratio ranging from about 5 to 250, although larger amounts in no way detract from satisfactorily conducting the distillation and carbonylation operations.

The process according to the present invention is particularly suitable for the carbonylation of conjugated dienes having the buta-1,3-diene skeleton in their molecule, such as:

(1) linear or branched chain aliphatic dienes containing from 4 to 12 carbon atoms and preferably from 4 to 8 carbon atoms, which are optionally substituted by inert groups such as: phenyl, cyclohexyl, nitro, oxo and alkoxycarbonyl; and (2) cyclic dienes containing from 6 to 8 carbon atoms.

Specific examples of conjugated dienes which are representative are buta-1,3-diene, isoprene, piperylene, hexa-1,3-diene, hexa-2,4-diene, chloroprene, 1-cyclohexyl-buta-1,3-diene, 1-phenylbuta-1,3-diene, octa-2,4-diene, 3-methylpenta-1,3-diene, 2-methylpenta-2,4-diene, cyclohexa-1,3-diene, cycloocta-1,3-diene and the like.

The alcohol which can be used to carry out the carbonylation operation is a linear or branched chain monoalcohol containing from 1 to 4 carbon atoms and preferably from 1 to 3 carbon atoms.

The halogenated hydracid employed is hydrochloric acid or hydrobromic acid, which can be introduced into the carbonylation medium in the gaseous form or in the form of an organic compound capable of releasing HCl or HBr in the medium, for example, in the form of 1-chlorobut-2-ene, 3-chlorobut-1-ene, 1-bromobut-2-ene or 3-bromobut-1-ene in the case of the carbonylation of butadiene. HCl and organic compounds capable of releasing HCl are preferred.

The following are exemplary of the palladium catalysts present during the carbonylation reaction:

(1) palladium metal deposited on a support, such as charcoal, alumina, silica or the like;

(2) palladium oxides;

(3) salts or complexes of palladium II in which the anion coordinated to the Pd cation is a "hard" or "intermediate" base, in particular the salts or the $\pi$-allyl complexes of Pd in which the anion coordinated to the Pd cation is selected from among the following anions: carboxylates, such as formate, acetate, propionate and benzoate; $SO_4{}^{2-}$; $NO_3{}^-$; acetylacetonate; and halides, such as $Cl^-$ and $Br^-$, and preferably $Cl^-$; or (4) complexes of palladium zero comprising organic ligands not containing elements of Group VB, representative of such complexes being bis-(dibenzalacetone)-Pd or bis-(cycloocta-1,5-diene)-Pd.

The amounts of reagents to be used in order to carry out the carbonylation operation can vary over very wide limits; it is obvious that the said amounts will be selected such that the process is economically advantageous.

Thus, although it is possible to use from 0.5 to 10 times the amount of alcohol required by stoichiometry, it is preferable, in order to attain maximum conversion of the conjugated diene while at the same time avoiding excessive dilution of the medium with alcohol, to carry out the process with a molar ratio alcohol/conjugated diene ranging from about 0.8 to 5 and preferably on the order of 1.

Likewise, the good activity of the palladium catalysts makes it possible to use the said catalysts in very small amounts (corresponding to a molar ratio conjugated diene/palladium on the order of 2,500); the use of a larger amount of catalyst (corresponding to a molar ratio conjugated diene/palladium on the order of 100) is not disadvantageous; as the desired object is to carry out a sufficiently rapid and selective carbonylation without consuming too much catalyst, a ratio conjugated diene/palladium ranging from about 100 and 2,000 is generally preferable.

The amount of halogenated hydracid to be used corresponds to a molar ratio halogenated hydracid/palladium of more than about 2. However, in order to avoid any risk of degradation of the alcohol to form alkyl halides and diaklyl ethers (this degradation being due to an excessive concentration of hydracid in the medium), a molar ratio halogenated hydracid/palladium ranging from about 2 to 100 and preferably ranging from about 5 to 60 will advantageously be selected.

As the object of the distillation operation is to separate the palladium catalyst from the principal product of the carbonylation reaction, namely, from the ester of the $\beta,\gamma$-unsaturated carboxylic acid corresponding to the diene and the alcohol employed, the conditions of temperature and pressure under which the distillation operation is carried out are adapted such as to vaporize the said ester of the $\beta,\gamma$-unsaturated carboxylic acid, the unreacted diene and alcohol and also the volatile products of low molecular weight, and such as to recover the palladium catalyst and the quaternary onium chloride or bromide in the liquid distillation residue containing the non-volatile products of high molecular weight.

"Volatile products of low molecular weight" are to be understood as connoting the organic products having a boiling point which is near or below that of the ester of the $\beta,\gamma$-unsaturated carboxylic acid obtained.

"Non-volatile products of high molecular weight" are to be understood as connoting those having a boiling point which is above that of the ester of the $\beta,\gamma$-unsaturated carboxylic acid obtained.

It is obvious that the distribution between "volatile products of low molecular weight" and "non-volatile products of high molecular weight" varies according to the nature of the starting material diene and alcohol.

Thus, if the selected diene and alcohol are butadiene and ethanol and the halogenated hydracid is HCl:

(a) the gas phase is constituted by, in particular, the following products: butadiene, butenes, chlorobutenes, ethoxybutenes, butadiene dimers (essentially 4-vinylcyclohexene), ethyl pentenoates, ethyl 2-methylbut-3-enoate, ethanol, HCl and ethyl chloride; and (b) the liquid distillation residue or distilland, is constituted by, in particular, the following products: carbonylated dimer (ethyl nona-3,8-dienoate), $C_6$ diesters (mostly diethyl 2-methylglutarate) and butadiene oligomers.

On the other hand, if the selected diene and alcohol are hexa-1,3-diene and ethanol, the distillation residue contains, inter alia, the diene dimer, because the latter is less volatile than the ester of the $\beta,\gamma$-unsaturated carboxylic acid obtained.

Likewise, it is possible that certain by-products of the carbonylation reaction will not be formed; thus, if the selected diene is isoprene, no formation of carbonylated dimer is observed.

The amount of quaternary onium chloride or bromide necessary for satisfactorily carrying out the distillation operation can be introduced into the reaction medium resulting from the carbonylation, either in total after the first carbonylation operation, or in portions during a series of carbonylation/distillation operations. As the presence of quaternary onium chlorides or bromides has a favorable effect during the carbonylation, it is advantageous to use all or a portion of the quaternary onium chloride or bromide during the carbonylation. In fact, it has been found (the subject of French Patent Application No. 81/01,205 filed Jan. 23, 1981, and assigned to the assignee hereof) that conjugated dienes can be carbonylated in the presence of an alcohol, a halogenated hydracid, a palladium catalyst and a quaternary onium chloride or bromide, in particular in the presence of the quaternary ammonium, phosphonium or arsonium chlorides or bromides utilized to carry out the distillation operation of the present invention; a beneficial effect, in particular on the degree of conversion of the dienes and the selectivity of the process in respect of the desired esters of $\beta,\gamma$-unsaturated carboxylic acids, has been found in the case of a molar ratio onium cation/palladium of at least 0.5 and very particularly ranging from 1 to 15; however, very much larger amounts of onium chloride or bromide are used to no disadvantage.

The operation for recycling the mixture of quaternary onium chloride or bromide and palladium catalyst, in the form of a homogeneous liquid, into the medium subjected to the carbonylation operation can be carried out by simple recycling, directly into the medium to be carbonylated, of the homogeneous liquid phase separated off during the distillation operation and comprising the said mixture of quaternary onium chloride or bromide and palladium catalyst, and of the non-volatile products of high molecular weight.

It too has been found that it is possible to carry out several successive cycles of carbonylation, distillation and recycling operations. The homogeneous liquid phase to be recycled becomes progressively richer in non-volatile products of high molecular weight, which gradually increases the volume of the liquid phase to be recycled. On an industrial scale, it is preferable not to have to recycle an excessive amount of liquid.

Another object of the present invention is to considerably broaden the limits of the above process, such limits being due to the presence of products of high molecular weight in the homogeneous liquid phase separated off by distillation, by subjecting the said homogeneous liquid phase to a treatment for total or partial removal of the products of high molecular weight, and by recycling the mixture of quaternary onium chloride or bromide and palladium catalyst, in the form of a homogeneous liquid, into the medium subjected to carbonylation.

The said treatment for removal of the products of high molecular weight can be carried out on all or a portion of the homogeneous liquid phase recovered (after distillation), either after each carbonylation/distillation cycle, or periodically after a series of carbonylation/distillation/recycling cycles.

The present invention also relates to the various methods of removing the products of high molecular weight and of recycling the mixture of quaternary onium chloride or bromide and palladium catalyst in the form of a homogeneous liquid.

The first method is a method of two-phase liquid-liquid separation, which comprises:

(i) contacting the homogeneous liquid phase, consisting of the mixture of quaternary onium chloride or bromide and palladium catalyst, and of the non-volatile products of high molecular weight, with an apolar aliphatic or cycloaliphatic hydrocarbon solvent, a polar solvent which is immiscible with the said apolar solvent and, if appropriate, an additional amount of quaternary onium chloride or brome, and permitting the resultant admixture to phase separate into a polar phase and an apolar phase;

(ii) decanting and separating said apolar phase containing the high molecular weight products to be recovered and said polar phase containing the mixture of quaternary onium chloride or bromide and palladium catalyst; and (iii) recycling, into the medium subjected to the carbonylation reaction, the mixture of quaternary onium chloride or bromide and palladium catalyst, either in the form of an alcoholic solution thereof or in the molten state after removal of the polar solvent; with said contacting step (i) being carried out with:

(1) an amount of quaternary onium chloride or bromide corresponding to a molar ratio quaternary onium cation/palladium of at least about 20; and (2) amounts of polar solvent and apolar hydrocarbon solvent which are at least equal to those required for the decantation of the contacting medium to form a polar phase and an apolar phase.

"Polar phase" is to be understood as connoting the phase in which the solvent comprises the polar solvent present during the contacting operation.

"Polar solvent which is immiscible with the apolar solvent" is to be understood as connoting solvents having a dielectric constant of more than about 20 (value measured at 20°–25° C.) and preferably of more than about 30, and providing a phase separation with the said apolar solvent, and also linear or branched chain aliphatic monoalcohols containing from 1 to 4 carbon atoms and preferably from 1 to 3 carbon atoms.

The following are exemplary of polar solvents which can be used: water ($\epsilon=78.4$); acetonitrile ($\epsilon=37.5$); N,N-dimethylformamide ($\epsilon=36.7$); dimethyl sulfoxide ($\epsilon=48$); nitromethane ($\epsilon=35.9$); N-methylpyrrolidone ($\epsilon=31$) and also methanol, ethanol, propanol or isopropanol.

In order to simplify the entirety of the process according to the present invention, the alcohol used to carry out the carbonylation will preferably be used as the polar solvent for carrying out the said contacting operation; the resulting alcoholic solution of quaternary onium chloride or bromide and palladium catalyst can be recycled directly into the medium subjected to the carbonylation operation.

However, it can be advantageous, for a better separation of the two phases, to carry out the contacting operation with the aid of an alcohol which is different from that used for the carbonylation operation, or with the aid of water or one of the non-alcoholic polar solvents mentioned above; it is then necessary to remove the solvent from the recovered polar phase by evaporation and, if appropriate, to dissolve the mixture of quaternary onium chloride or bromide and palladium catalyst in the alcohol used to carry out the next carbonylation operation.

"Apolar phase" is to be understood as connoting the phase in which the solvent comprises the apolar aliphatic or cycloaliphatic hydrocarbon solvent present during the contacting operation.

"Apolar aliphatic or cycloaliphatic hydrocarbon solvent" is to be understood as connoting aliphatic or cycloaliphatic hydrocarbons having a dielectric constant of less than 2.3 (value measured at 20°–25° C.) and very particularly of less than 2.1 (at 20°–25° C.). The following are exemplary of such solvents: pentane ($\epsilon=1.84$), isopentane ($\epsilon=1.84$), hexane ($\epsilon=1.89$), cyclohexane ($\epsilon=2.02$), octane ($\epsilon=1.95$), isooctane ($\epsilon=1.94$), cyclooctane ($\epsilon=1.95$), decane ($\epsilon=1.99$), dodecane ($\epsilon=2.01$), tetradecane, hexadecane or their mixtures of the petroleum ether type.

The degree of separation of the polar phase from the apolar phase is the greater:

(a) the higher the molar ratio quaternary onium cation/palladium;

(b) the higher the weight ratio quaternary onium chloride or bromide/polar solvent; and (c) the greater the difference between the dielectric constant of the polar solvent and that of the apolar hydrocarbon solvent.

It is obvious that it is not economically advantageous to use too large an excess of quaternary onium chloride or bromide or to use excessive amounts of polar solvent.

In general, the contacting operation can advantageously be carried out in the presence of:

(1) an amount of quaternary onium chloride or bromide corresponding to a molar ratio onium cation/palladium ranging from about 20 to 300 and preferably ranging from 30 to 200;

(2) an amount of polar solvent corresponding to a weight ratio quaternary onium chloride or bromide/polar solvent of at least about 0.1, preferably ranging from 0.25 to 30 and very particularly ranging from 0.3 to 20; and (3) an amount of apolar hydrocarbon solvent corresponding to a weight ratio apolar hydrocarbon solvent/polar solvent of more than 1, preferably of more than about 2 and very particularly of more than 3.

If desired, a more thorough removal of the products of high molecular weight can be achieved by subjecting the polar phase obtained after decantation to a complementary treatment comprising subjecting the said polar phase to one or more extraction and separation operations with the aid of the apolar hydrocarbon solvent.

The contacting operation is carried out under temperature conditions which make it possible to obtain a good separation of the two phases, and to do this in an economically advantageous manner. The relative miscibility of a polar solvent with an apolar solvent generally decreases with decreasing temperature; it has been found that the solubility of the quaternary onium chloride or bromide in the polar solvent also decreases, but that it nevertheless remains high; thus, the contacting operation can be carried out at low temperature and preferably at a temperature close to ambient temperature.

The second method of removing the products of high molecular weight and of recycling the mixture of quaternary onium chloride or bromide and palladium catalyst is a method of solid-liquid separation, which comprises:

(i) contacting the constituents of the homogeneous liquid phase, separated off during the distillation operation, with an apolar aliphatic or cycloaliphatic hydrocarbon solvent at a temperature which is below or equal to the solidification temperature of the homogeneous liquid phase;

(ii) subjecting the solid-liquid system obtained to a filtration operation;

(iii) removing the solution of non-volatile products of high molecular weight in the said apolar solvent;

(iv) converting the filtration residue, comprising a mixture of quaternary onium chloride or bromide and palladium catalyst, to a homogeneous liquid by melting or by dissolution in an alcohol, perferably in the alcohol utilized during the carbonylation operation; and (v) recycling the said homogeneous liquid obtained into the medium subjected to the carbonylation reaction.

The said contacting step (i) according to this second method can be carried out:

(a) preferably, by cooling the homogeneous liquid phase, separated off by distillation, until the mixture of quaternary onium chloride or bromide and palladium catalyst crystallizes, and by treating the resulting medium with an amount of the apolar solvent which is at least sufficient to dissolve the non-volatile products of high molecular weight; or (b) by treating the homogeneous liquid phase, separated off by distillation, with an amount of the apolar solvent which is at least sufficient to dissolve the non-volatile products of high molecular weight, and by cooling the resulting medium until the mixture of quaternary onium chloride or bromide and palladium catalyst crystallizes.

The apolar aliphatic or cycloaliphatic hydrocarbon solvents used are those already mentioned above for carrying out the contacting step in accordance with the first method of removing the products of high molecular weight (namely, in accordance with the method of two-phase liquid-liquid separation).

This second method of removing the products of high molecular weight and of recycling the mixture of quaternary onium chloride or bromide and palladium catalyst is particularly suitable for the treatment of homogeneous liquid distillation residues containing only a limited amount of non-volatile products of high molecular weight, for example, not more than 10% by volume, when the selected diene is butadiene and when the quaternary onium salt used is tetrabutylphosphonium chloride.

The individual entities corresponding to the term "mols" are as follows:

(1) Alcohol: gram molecule
(2) Conjugated diene: gram molecule
(3) Halogenated hydracid: gram molecule
(4) Palladium: gram atom
(5) Quaternary onium cation: gram ion In order to further illustrate the present invention and the advantages thereof, the following specific examples are given, it being understood that same are intended only as illustrative and in nowise limitative.

The abbreviations indicated in the tables which follow corresponding to noted examples have the following meanings:

Ex: example;
BD: butadiene;
ROH: alcohol; Me: methyl; Et: ethyl; Bu: n-butyl
Dod: dodecyl;
Pd(DBA)$_2$: bis-(dibenzalacetone)-Pd;
[<(Pd-Cl]$_2$: bis-($\pi$-allyl-chloropalladium);
catalyst: palladium catalyst;
co-catalyst: HCl or reaction product of HCl+conjugated diene employed;
onium: quaternary onium salt;
polar: polar solvent;
alkane: apolar hydrocarbon solvent;
AN: acetonitrile;
DMF: N,N-dimethylformamide;
RM: reaction mass resulting from the carbonylation (containing the unconverted butadiene together with volatile products which evaporate during the subsequent contacting operation carried out at ambient temperature);
P$_3$: pent-3-enoic acid ester;
P$_4$: pent-4-enoic acid ester;
P$_2$: pent-2-enoic acid ester;
P': 2-methylbut-3-enoic acid ester;
C$_9$: nona-3,8-dienoic acid ester;
C$_6$: C$_6$ dialkyl esters (mostly dialkyl 2-methylglutarate);
HC$_8$: butadiene dimers (essentially 4-vinylcyclohexene);
PA: pentanoic acid ester and 2-methylbutanoic acid ester;
ROC$_4$: 3-alkoxybut-1-ene and 1-alkoxybut-2-ene;
ClC$_4$: 3-chlorobut-1-ene and 2-chlorobut-2-ene;

ClPA: chloropentanoic acid ester;
Cl: alkyl chloride and dialkyl ether (side reaction of HCl with the alcohol);
DC: overall degree of conversion of the butadiene (in mol %);
RY: partial degree of conversion (in mol %) for each product obtained, relative to the butadiene introduced, with $DC = \Sigma_i RY_i$.
In the calculation of DC, only the RY of the following products are taken into account: $P_3$, $P_4$, $P_2$, $P'$, $C_9$, $C_6$, $HC_8$, PA, $ROC_4$ and ClPA; in effect, the chlorobutenes ($ClC_4$) are equivalent to a mixture of butadiene + HCl, which can be carbonylated to $P_3$.
S: selectivity (in mol %) for each product, with $S = RY/DC$;
RYCl: partial degree of conversion (in mol %) to ethyl chloride and diethyl ether, relative to the ethanol introduced;
RYBr: partial degree of conversion (in mol %) to ethyl bromide and diethyl ether;
A: specific activity of the catalyst, expressed as the number of mols of $P_3$ obtained per g atom of Pd and per hour, more than 95% of the linear pentenoic acid esters obtained consisting of $P_3$;
CO: technical-grade CO gas containing about 0.8% by volume of hydrogen, which does not have an appreciable effect on the carbonylation reaction.

EXAMPLE 1

(1a) Carbonylation Step

The following materials were introduced, under a stream of argon, into a 125 cm³ autoclave made of nickel-molybdenum alloy marketed under the trademark HASTELLOY $B_2$:

(i) 0.0774 g (namely, 0.2115 millimol) of anhydrous bis-($\pi$-allyl-chloropalladium) (0.423 mg atom of Pd);

(ii) 12.5 g (namely, 42.2 millimols) of tetrabutylphosphonium chloride, which corresponds to a molar ratio $PBu_4^+Cl^-/Pd$ of 100;

(iii) 12 g (namely, 261 millimols) of ethanol; and (iv) 0.19 g (namely, 2.12 millimols) of 1-chlorobut-2-ene, which corresponds to a molar ratio HCl/Pd of 5.

The autoclave was closed; 14.5 g (namely, 268.5 millimols) of butadiene were transferred therein, which corresponds to a molar ratio butadiene/Pd of 635 and a molar ratio alcohol/butadiene of 1.

The autoclave which was agitated by shaking, was heated to 120° C. and charged with CO at a constant total pressure of 196 bars.

The reaction was permitted to proceed for 2 hours at this temperature. The autoclave was then cooled to 150° C. and degassed slowly.

The reaction conditions are summarized in Table IA.

41.17 g of a green-yellow homogeneous solution, containing 5.2% by weight of ethanol and 61.2% by weight of ethyl pentenoates, were recovered.

Table IIA reports the results of gas chromatographic analysis of the solution obtained, together with the S and RY corresponding to each product formed.

The overall degree of conversion of the butadiene, DC, was 80.7 mol %.

The specific activity A of the catalyst was 232 hour$^{-1}$.

The green-yellow homogeneous solution resulting from this step (1a) was separated into fractions, namely, a 20 g fraction to be subjected to a distillation operation (1b), and a 51.1 g fraction to be subjected to a distillation operation (1d).

(1b) Distillation Step (The conditions and the results of the distillation are summarized in Table IIIA).

20 g of the yellow solution obtained, containing 60.5 g of tetrabutylphosphonium chloride, were taken and subjected to distillation at a temperature of 84° C. and under an absolute pressure of 3,500 Pa. This provided an amount of 10.80 g of distillation condensate which was free of Pd and contained 10.3 g of ethyl pent-3-enoate, and 7.5 g of a distillation residue, which was a clear homogeneous orange liquid. This residue contained all of the palladium catalyst and the tetrabutylphosphonium chloride used, namely:

(1) 21.9 mg (0.206 mg atom) of Pd; and (2) 6.05 g (20.51 millimols) of phosphonium chloride.

(1c) Recycling into the carbonylation autoclave

A carbonylation step was carried out under the conditions described in step (1a), starting from:

(i) 7.5 g of liquid distillation residue from step (1b);

(ii) 0.0933 g (namely, 1.03 millimols) of 1-chlorobut-2-ene, which corresponds to a molar ratio HCl/Pd of 5;

(iii) 6 g (130.4 millimols) of ethanol; and (iv) 6 g (111.2 millimols) of butadiene, which corresponds to a molar ratio butadiene/Pd of 540 and a molar ratio alcohol/butadiene of 1.17.

After a carbonylation reaction time of two hours at 120° C. under 196 bars, 19.02 g of a green solution, containing 4.6% by weight of ethanol and 61% by weight of ethyl pentenoate, were recovered.

Table IIA reports the results of gas chromatographic analysis of the solution obtained, together with the S and RY corresponding to each product formed.

The overall degree of conversion of the butadiene, DC, was 86.5 mol %.

The specific activity A of the catalyst was 222 hour$^{-1}$.

It was found that there had been no loss of catalyst and that its activity had been retained.

(1d) Distillation Step 15.1 g of the green-yellow solution obtained in carbonylation step (1a), containing 4.55 g of tetrabutylphosphonium chloride, were taken and subjected to distillation at a temperature of 84° C. and under a pressure of 3,100 Pascals. This provided an amount of 8.4 g of distillation condensate and 4.95 g of an orange liquid distillation residue containing:

(1) 16.5 mg (namely, 0.155 mg atom) of Pd; and (2) 4.55 g (namely, 15.4 millimols) of phosphonium chloride.

(1e) Extraction of the products of high molecular weight (The conditions and the results of the extraction are summarized in Table IV.)

40 g of n-hexene and 13 g of methanol were added to the distillation residue from step (1d).

The composition thus obtained contained:

(1) 22.4% by weight of methanol, which corresponds to a weight ratio apolar solvent/alcohol of 3:1, and (2) 7.9% by weight of $PBu_4^+Cl^-$, which corresponds to a molar ration $PBu_4^+Cl^-/Pd$ of 100 and a weight ratio $PBu_4^+Cl^-$/alcohol of 0.35.

The medium separated into two phases: (a) a colorless upper phase (41.1 g) containing the hexane, the ethyl nona-3,8-dienoate and the $C_6$ diesters, and less than 4 ppm of Pd; and (b) a yellow lower phase (16.8 g) containing the methanol and more than 99.4% of the phosphonium salt and of the palladium catalyst.

It was found that there had been a virtually total separation of the palladium catalyst from all of the carbonylation reaction products (of low molecular weight and high molecular weight).

The methanol contained in the yellow lower phase was then removed by distillation; this provided a homogeneous residue, which was recycled in the molten state into the carbonylation autoclave.

It was found that direct recycling of the distillation residue (steps 1b and 1c) makes it possible to recycle all of the catalyst without removing the reaction products of high molecular weight, whereas recycling after a two-phase extraction operation (step 1e) makes it possible to recycle the catalyst with a minimum loss of catalyst and virtually total removal of the reaction products of high molecular weight.

EXAMPLE 2

(2a) Carbonylation Step

The following materials were introduced, under a stream of argon, into a 125 cm$^3$ autoclave made of nickel-molybdenum alloy marketed under the trademark HASTELLOY $B_2$:

(i) 0.150 g (namely, 0.845 millimol) of anhydrous palladium(II) chloride;

(ii) 24 g (namely, 522 millimols) of ethanol; and (iii) 1.54 g (namely, 42.2 millimols) of gaseous HCl, which corresponds to a molar ration HCl/Pd of 50.

The autoclave was closed; 23 g (namely, 426 millimols) of butadiene were transferred therein, which corresponds to a molar ratio butadiene/Pd of 500 and a molar ratio alcohol/butadiene of 1.

The autoclave, which was agitated by shaking, was heated to 120° C. and charged with CO at a constant total pressure of 145 bars.

The reaction was permitted to proceed for 2 hours at this temperature. The autoclave was then cooled to 15° C. and degassed slowly.

The reaction conditions are summarized in Table IA.

46.6 g of a yellow homogeneous solution, containing 28% by weight of ethanol and 56% by weight of ethyl pentenoates, were recovered.

Table IIA reports the results of gas chromatographic analysis of the solution obtained, together with the S and RY corresponding to each product formed.

The overall degree of conversion of the butadiene, DC, was 53.9 mol %.

The specific activity A of the catalyst was 121 hour$^{-1}$.

(2b) Distillation Step

An amount of 3 g (namely, 10.17 millimols) of tetrabutylphosphonium chloride was added to a 19.63 g sample of the reaction mass, containing 37.9 mg (namely, 0.356 mg atom) of Pd, which corresponds to a molar ratio onium/Pd of 28.

This homogeneous mixture was subjected to distillation at a temperature of 85° C. and under an absolute pressure of 3,500 Pa. The following were collected: 11.3 g of distillation condensate containing 86% of pent-3-enoic acid ester (namely, 9.7 g), and 3.69 g of a clear homogeneous red liquid residue containing all of the Pd catalyst and all of the phosphonium salt, namely:

(1) 37.9 mg (namely, 0.356 mg atom) of Pd; and (2) 3 g (namely, 10.2 millimols) of PBu$_4$Cl, which corresponds to a molar ratio onium/Pd of 28.

(2c) Recycling into the carbonylation autoclave

A carbonylation step was carried out under the conditions described in step (2a), starting from:

(i) 3.69 g of liquid distillation residue;

(ii) 1.91 g (21.15 millimols) of 1-chlorobut-2-ene;

(iii) 12 g (126 millimols) of ethanol; and (iv) 14 g (259 millimols) of butadiene, which corresponds to a molar ratio butadiene/Pd of 728 and a molar ratio alcohol/butadiene of 1.

After a carbonylation time of two hours at 120° C. under 145 bars, 27.3 g of a homogeneous green solution were recovered.

(2d) Distillation Step

An additional 3 g (namely, 10.17 millimols) of tetrabutylphosphonium chloride were added to the entirety of the reaction mass obtained in carbonylation step (2c) (namely, 27.3 g), which corresponds to a molar ratio onium/Pd of 56. The mixture was subjected to a distillation operation under the conditions indicated in Table IIIA. The following were collected:

(1) 13.7 g of distillation condensate containing 56% of pent-3-enoic acid ester (namely, 7.7 g); and (2) 7.29 g of clear, homogeneous, dark orange liquid residue containing: (2a) 37.9 mg (namely, 0.356 mg atom) of Pd; and (2b) 6 g (namely 20.3 millimols) of tetrabutyphosphonium chloride.

(2e) Recycling into the carbonylation autoclave

A carbonylation step was carried out under the cconditions described in step (2a), using the distillation residue from step (2d) and the amounts of starting materials indicated in Table IA.

33.7 g of a homogeneous green solution were recovered.

(2f) Distillation Step

The 33.7 g of green solution obtained in step (2e) were subjected to a distillation operation under the conditions indicated in Table IIIA.

20.3 g of distillation condensate containing 10.2 g of pent-3-enoic acid esters, and 8.20 g of a clear homogeneous orange-brown liquid residue, were collected.

(2g) Recycling into the carbonylation autoclave

A carbonylation step was carried out under the conditions indicated in step (2a), using the distillation residue from step (2f) and the amounts of starting materials indicated in Table IA.

33.7 g of a homogeneous green solution were recovered.

(2h) Distillation Step

The 33.7 g of green solution obtained in step (2g) were subjected to a distillation operation under the conditions described in Table IIIA.

The following were collected:

(1) 21.2 g of distillation condensate containing 10.7 g of pent-3-enoic acid esters; and (2) 8.50 g of a clear homogeneous orange-brown liquid residue.

This residue, weighing 8.50 g, contained all of the Pd catalyst and all of the phosphonium salt, namely:

(1) 37.9 mg (namely, 0.356 mg atom) of Pd; (2) 6 g (namely, 20.3 millimols) of tetrabutylphosphonium chloride, which corresponds to a molar ratio $PBu_4^+Cl^-/Pd$ of 56; and (3) 2.4 g of organic products, which were, in particular, non-volatile products of high molecular weight, such as the nona-3,8-dienoate and the $C_6$ diesters.

(2i) Extraction of the products of high molecular weight

The following materials were added to the distillation residue from step (2h):

(i) 33.4 g of n-octane; and (ii) 4.4 g of ethanol, which corresponds to a weight ratio $PBu_4^+Cl^-$/ethanol of 1.4 and a weight ratio octane/ethanol of 7.6.

The medium separated into two phases:

(a) a colorless upper phase (33.7 g) containing the octane, the ethyl nona-3,8-dienoate and the $C_6$ diesters, and less than 7 ppm of Pd; and (b) a viscous yellow lower phase (12.6 g) containing the residual ethanol, more than 99.6% of the Pd catalyst and more than 99.5% of the onium.

The conditions and the results of this extraction step are indicated in Table IV.

(2j) Recycling into the carbonylation autoclave

A carbonylation step was carried out under the conditions described in step (2a), using the 12.6 g of yellow alcohol phase obtained in extraction step (2i) and the amounts of starting materials indicated in Table IA.

32.5 g of homogeneous, light green solution were recovered.

(2k) Distillation Step

The 32.5 g of light green solution obtained in step (2j) were subjected to a distillation operation under the conditions indicated in Table IIIA.

The following were collected:

(1) 18.7 g of distillation condensate containing 9.6 g of pent-3-enoic acid ester; and (2) 7.2 g of a clear homogeneous green liquid residue containing 0.335 mg atom of Pd and 20.3 millimols of tetrabutylphosphonium chloride.

In the same series of recycling experiments (2e), (2g) and (2j), which were carried out under identical conditions: (i) same amounts of catalyst and tetrabutylphosphonium chloride; (ii) same temperature and pressure; and (iii) identical carbonylation times; it was found that the amount of ethyl pent-3-enoate produced remained approximately constant and close to 10 g, which indicated that the activity of the catalyst was constant and did not deteriorate during successive recycles.

EXAMPLE 3

(3a) Carbonylation Step

The following materials were introduced, under a stream of argon, into a 125 cm³ autoclave made of nickel-molybdenum alloy marketed under the trademark HASTELLOY B2.

(i) 1.725 g (namely, 3.0 millimols) of bis(dibenzalacetone)-Pd;

(ii) 7.08 g (namely, 23.9 millimols) of tetrabutylphosphonium chloride, which corresponds to a molar ratio $PBu_4^+Cl^-/Pd$ of 8;

(iii) 23.0 g (namely, 500 millimols) of ethanol; and (iv) 5.43 g (namely, 60.0 millimols) of 1-chlorobut-2-ene, which corresponds to a molar ratio HCl/Pd of 20.

The autoclave was closed; 23 g (namely, 426 millimols) of butadiene were transferred therein, which corresponds to a molar ratio butadiene/Pd of 142 and a molar ratio alcohol/butadiene of 1.17.

The autoclave, which was agitated by shaking, was heated to 120° C. and charged with CO at a constant total pressure of 120 bars.

The reaction was permitted to proceed for 2 hours at this temperature. The autoclave was then cooled to 15° C. and degassed slowly.

53.9 g of a homogeneous, light red solution, containing 23% by weight of ethanol and 36% by weight of ethyl pentenoates, were recovered.

Table II reports the results of gas chromatographic analysis of the solution obtained, together with the S and RY corresponding to each product formed.

The overall degree of conversion of the butadiene, DC, was 42.4 mol %.

The specific activity A of the catalyst was 22.4 $hour^{-1}$.

(3b) Distillation Step 51.6 g of the clear homogeneous red solution obtained in carbonylation step (3a) were subjected to a distillation operation at a temperature of 76° C. and under a pressure of 3,500 Pascals. This provided:

(1) 28.4 g of distillation condensate containing 16.2 g of pentenoic acid esters; and (2) 10.25 g of homogeneous, dark red liquid residue containing:

(2a) 305 mg (namely, 2.87 mg atoms) of Pd;

(2b) 6.8 g (namely, 23 millimols) of tetrabutylphosphonium chloride; and (2c) 0.73 g of the non-volatile organic products consisting of nona-3,8-dienoate and $C_6$ diesters.

(3c) Recycling into the Carbonylation Autoclave

A carbonylation step was carried out under the conditions described in step (3a), using 10.25 g of dark red liquid residue obtained in distillation step (3b) and the amounts of starting materials indicated in Table IA.

46.35 g of a homogeneous red solution were recovered, the composition of which is indicated in Table II.

EXAMPLE 4

(4a) Carbonylation Step

The following materials were introduced, under a stream of argon, into a 125 cm³ autoclave made of nickel-molybdenum alloy marketed under the trademark HASTELLOY B2:

(i) 0.1064 g (namely, 0.60 millimol) of $PdCl_2$;

(ii) 4.425 g (15 millimols) of $PBu_4^+Cl^-$, which corresponds to a ratio $PBu_4Cl/Pd$ of 25;

(iii) 18.4 g (400 millimols) of ethanol; and (iv) 2.716 g (30 millimols) of 1-chlorobut-2-ene, which corresponds to a molar ratio HCl/Pd of 50.

The autoclave was closed; 21.5 g (398 millimols) of butadiene were transferred therein, which corresponds to a molar ratio butadiene/Pd of 713 and a molar ratio alcohol/butadiene of 1.

The autoclave was heated to 120° C. and charged with CO at a constant total pressure of 130 bars.

The reaction was permitted to proceed for 4 hours, 30 minutes and the autoclave was then cooled and degassed.

The reaction conditions are summarized in Table IB.

53.1 g of a homogeneous, light green solution were recovered, the analysis of which is set forth in Table II.

The overall degree of conversion of the butadiene, DC, was 70.5 mol %.

The specific activity A of the catalyst was 85 hour$^{-1}$.

(4b) Distillation Step 50.6 g of the reaction was obtained in carbonylation step (4a) were subjected to a distillation operation of 86° C. under 3,500 Pa.

The following were collected:

(1) 28.7 g of distillation condensate containing 93% of ethyl pentenoates; and (2) 7.40 g of clear homogeneous orange-brown liquid residue containing:

(2a) 4.22 g (14.3 millimols) of PBu$_4$Cl;

(2b) 60.8 mg (0.571 mg atom) of Pd;

(2c) 0.99 g of ethyl nonadienoate; and (2d) 1.16 g of C$_6$ diesters.

(4c) Recycling into the Carbonylation Autoclave

A carbonylation step was carried out under the conditions described in step (4a), using the 7.40 g of orange-brown distillation residue from step (4b) and the amounts of raw materials indicated in Table IB.

40.61 g of a homogeneous green solution were recovered, the analysis of which is set forth in Table II.

(4d) Distillation Step 39.6 g of the green solution obtained in carbonylation step (4c) were subjected to a distillation step under the conditions indicated in Table IIIA.

The following were collected:

(1) 18.80 g of distillation condensate containing 86% of ethyl pentenoates; and (2) 8.40 g of homogeneous brown-red liquid residue containing:

(2a) 4.11 g (14 millimols) of PBu$_4$Cl; and (2b) 59.3 mg (0.56 millimols) of Pd.

(4e) Recycling into the Carbonylation Autoclave

A carbonylation step was carried out under the conditions described in step (4a), using 8.40 g of brown-red liquid distillation residue from step (4d) and the amounts of raw materials indicated in Table IB.

A large amount of PBu$_4$Cl was introduced (42.1 millimols) in order to provide a molar ratio onium/Pd of 100.

67.2 g of a homogeneous green solution were recovered, the analysis of which is reported in Table II.

EXAMPLE 5

(5a) Carbonylation Step

The following materials were introduced, under a stream of argon, into a 125 cm$^3$ autoclave made of nickel-molybdenum alloy marketed under the trademark HASTELLOY B2.

(i) 0.0385 g (namely, 0.217 millimol) of palladium chloride:

(ii) 12.46 g (namely, 42.25 millimols) of tetrabutylphosphonium chloride, which corresponds to a molar ratio PBu$_4$+Cl$^-$/Pd of 200;

(iii) 12.0 g (namely, 261 millimols) of ethanol; and (iv) 0.957 g (namely, 10.5 millimols) of 1-chlorobut-2-ene, which corresponds to a molar ratio HCl/Pd of 50.

The autoclave was closed; 15 g (namely, 278 millimols) of butadiene were transferred therein, which corresponds to a molar ratio butadiene/Pd of 1,300 and a molar ratio alcohol/butadiene of 0.94.

The autoclave, which was agitated by shaking, was heated to 140° C. and charged with CO at a constant total pressure of 145 bars.

The reaction was permitted to proceed for 1 hour, 20 minutes at this temperature. The autoclave was then cooled to 15° C. and degassed slowly.

The reaction conditions are reported in Table IB.

47.8 g of a homogeneous green solution, containing 5% by weight of ethanol and 48% by weight of ethyl pentenoates, were recovered.

Table II reports the results of gas chromatographic analysis of the solution obtained, together with the S and RY corresponding to each product formed.

The overall degree of conversion of the butadiene, DC, was 73.1 mol %.

The specific activity A of the catalyst was 608 hour$^{-1}$.

(5b) Distillation Step 40.7 g of the reaction mass obtained in step (5a), containing 10.6 g of tetrabutylphosphonium chloride, were taken and subjected to a distillation operation at a temperature of 76° C. and under a pressure of 3,500 Pa.

This provided an amount of 22.7 g of distillate and 14.5 g of an orange-yellow liquid distillation residue containing:

(1) 19.6 mg (namely, 0.184 mg atom) of palladium; and (2) 10.6 g (namely, 38 millimols) of tetrabutylphosphonium chloride.

(5c) Recycling into the Carbonylation Autoclave

A carbonylation step was carried out under conditions similar to those of step (5a), recycling the 14.5 g of liquid distillation residue from step (5b) and using the amounts of starting materials indicated in Table IB.

This carbonylation step was carried out for 1 hour at a temperature of 140° C. and under a pressure of 145 bars.

39.8 g of homogeneous green solution, containing 13.8% by weight of ethanol and 33% by weight of ethyl pentenoates, were recovered. The results of the chromatographic analysis of the said solution are indicated in Table II.

(5d) Distillation Step 39.2 g of the reaction mass obtained in step (5c) were subjected to a distillation operation at a temperature of 80° C. and under a pressure of 3,500 Pa.

The following were collected:

(1) 22.2 g of distillation condensate; and (2) 13.9 g of orange liquid distillation residue containing:

(2a) 10.4 g (37.5 millimols) of phosphonium chloride;

(2b) 19.6 mg (0.184 mg atom) of Pd; and (2c) about 1.9 g of reaction products of high molecular weight.

(5e) Extraction of the Products of High Molecular Weight 3.6 g of ethanol and 15 g of 2,2,4-trimethylpentane (isooctane) were added to the 13.9 g of orange distillation residue from step (5d).

The composition thus obtained contained:

(1) 11.1% by weight of ethanol, which corresponds to a weight ratio apolar solvent/alcohol of about 4.2.

(2) 32.0% by weight of $PBu_4Cl$, which corresponds to a molar ratio $PBu_4Cl/Pd$ of 200 and a weight ratio $PBu_4Cl$/ethanol of 2.9.

The medium separated into two phases:

(a) a colorless upper phase (17.9 g) containing isooctane and:

more than 80% of the organic products of high molecular weight; less than 2.5 ppm of Pd;

less than 50 ppm of P; and (b) a yellow lower phase (14.5 g) containing the ethanol, 99.8% of the Pd and more than 99.8% of the $PBu_4Cl$.

The conditions and the results of this extraction step are summarized in Table IV.

The yellow ethanol phase was then recycled into the carbonylation autoclave for a further carbonylation operation.

EXAMPLE 6

(6a) Carbonylation Step

The following materials were introduced, under a stream of argon, into a 125 cm$^3$ autoclave made of nickel-molybdenumalloy marketed under the trademark HASTELLOY B$_2$:

(i) 0.225 g (namely, 1.268 millimols) of $PdCl_2$;

(ii) 12.46 g (namely, 42.25 millimols) of tetrabutylphosphonium chloride, which corresponds to a molar ratio $PBu_4^+Cl^-/Pd$ of 33;

(iii) 8.00 g (namely, 250 millimols) of methanol; and (iv) 3.86 g (namely, 42.2 millimols) of 1-chlorobut-2-ene, which corresponds to a molar ratio HCl/Pd of 33.

The autoclave was closed; 14 g (namely, 259 millimols) of butadiene were transferred therein, which corresponds to a molar ratio butadiene/Pd of 205 and a molar ratio alcohol/butadiene of 0.96.

The autoclave, which was agitated by shaking, was heated to 100° C. and charged with CO at a constant total pressure of 120 bars. The reaction was permitted to proceed for 2 hours at this temperature. The autoclave was then cooled to 15° C. and degassed slowly.

The reaction conditions are summarized in Table IC. 33.0 g of a homogeneous green solution, containing 15.4% by weight of methanol and 38.3% by weight of methyl pentenoates, were recovered.

Table IIA reports the results of gas chromatographic analysis of the solution obtained, together with the S and RY corresponding to each product formed.

The overall degree of conversion of the butadiene, DC, was 45.5 mol %.

The specific activity A of the catalyst was 44 hour$^{-1}$.

(6b) Distillation Step

The reaction mass of step (6a) was subjected to a distillation operation at a temperature of 85° C. and under an absolute pressure of 4,700 Pascals. The following were collected: 16.9 g of distillation condensate containing 12.3 g of methyl pent-3-enoate, and 13 g of orange liquid residue containing all of the Pd and all of the phosphonium salt.

(6c) Recycling into the Carbonylation Autoclave

A carbonylation operation was carried out under conditions similar to those of step (6a), recycling 12.5 g of the orange liquid residue obtained in distillation step (6b) and using the amounts of starting materials indicated in Table IC.

This carbonylation step was carried out for 2 hours at 100° C. and under 120 bars.

30.3 g of a homogeneous green solution, containing 15.7% by weight of methanol and 36.7% by weight of methyl pentenoates, were recovered. The results of chromatographic analysis of the said solution are reported in Table IIA.

EXAMPLE 7

(7a) Carbonylation Step

The following materials were introduced, under a stream of argon, into a 125 cm$^3$ autoclave made of nickel-molybdenum alloy marketed under the trademark HASTELLOY B$_2$:

(i) 0.15 g (namely, 0.845 millimol) of palladium chloride;

(ii) 24 g (namely, 522 millimols) of ethanol; and (iii) 1.54 g (namely, 42.2 millimols) of gaseous hydrochloric acid, which corresponds to a molar ratio HCl/Pd of 50.

The autoclave was closed; 24 g (namely, 444.4 millimols) of butadiene were transferred therein, which corresponds to a molar ratio butadiene/Pd of 525 and a molar ratio alcohol/butadiene of 1.

The autocalve, which was agitated by shaking, was heated to 120° C. and charged with CO at a constant total pressure of 145 bars. The reaction was permitted to proceed for 2 hours at this temperature. The autoclave was then cooled to 15° C. and degassed slowly.

The reaction conditions are summarized in Table IC.

52.6 g of a homogeneous yellow solution, containing 23.9% by weight of ethanol and 54.1% by weight of ethyl pentenoates, were recovered.

Table IIA reports the results of gas chromatographic analysis of the solution obtained, together with the S and RY corresponding to each product formed.

The overall degree of conversion of the butadiene, DC, was 54.3 mol %.

The specific activity A of the catalyst was 132 hour$^{-1}$.

(7b) Distillation Step

An amount of 8.08 g (namely, 27.4 millimols) of tetrabutylphosphonium chloride was added to 17 g of the reaction mass obtained in step (7a), containing 4.05 g of ethanol and 9.19 g of pentenoic acid esters, which corresponds to a molar ratio onium/Pd of 100.

This homogeneous mixture was subjected to distillation at 76° C. and under a pressure of 3,500 Pascals. 10.33 g of distillation condensate consisting mainly of pentenoic acid esters, and 8.55 g of viscous, dark yellow residue, were collected.

The said viscous residue was a homogeneous solution, which solidified on cooling; it consisted of:

(1) 8.08 g (27.4 millimols) of $PBu_4Cl$;

(2) 29.4 mg (0.276 mg atom) of Pd; and (3) 0.42 g of organic products.

(7c) Extraction of the Products of High Molecular Weight 15 ml of octane were added to the said residue and the mixture was then filtered. The crystalline residue obtained was subsequently washed with 5 ml of octane and then dried; the crystalline solid obtained (8.15g) was orange; it contained 99.9% of the palladium catalyst and of the tetrabutylphosphonium chloride used; the said solid, which was soluble in ethanol, was taken up for a further carbonylation step.

The octane filtrate contained 85% of the ethyl nonadienoate present in the reaction mixture obtained in step (7a) and 2.1 ppm of palladium.

EXAMPLE 8

(8a) Carbonylation Step

The following materials were introduced, under a stream of argon, into a 125 cm$^3$ autoclave made of nickel-molybdenum alloy marketed under the trademark HASTELLOY B$_2$:

(i) 0.075 g (namely, 0.423 millimol) of PdCl$_2$;

(ii) 16.4 g (about 40.6 millimols) of a quaternary onium chloride having the trademark ALIQUAT 336, marketed by General Mills and consisting mainly of trioctylmethylammonium chloride, which corresponds to a molar ratio onium/Pd of about 96; p (iii) 12 g (namely, 261 millimols) of ethanol; and (iv) 1.9 g (namely, 21.2 millimols) of 1-chloro-but-2-ene, which corresponds to a molar ratio HCl/Pd of 50.

The autocalve was closed; 14 g (namely, 259 millimols) of butadiene were transferred therein, which corresponds to a molar ratio butadiene/Pd of 613 and a molar ratio alcohol/butadiene of 1.

The autoclave, which was agitated by shaking, was heated to 120° C. and charged with CO at a constant total pressure of 145 bars. The reaction was permitted to proceed for 2 hours at this temperature. The autoclave was then cooled to 150° C. and degassed slowly.

The reaction conditions are summarized in Table IC.

47.5 g of a homogeneous yellow solution, containing 9% by weight of ethanol and 37% by weight of ethyl pentenoates, were recovered.

Table IIA reports the results of gas chromatographic analysis of the solution obtained, together with the S and RY corresponding to each product formed.

The overall degree of conversion of the butadiene, DC, was 58.9 mol %.

The specific activity A of the catalyst was 163 hour$^{-1}$.

(8b) Distillation Step 46.7 g of the yellow reaction mass obtained in step (8a) were subjected to a distillation operation at a temperature of 74° C. and under an absolute pressure of 3,500 Pascals. The following were collected: 22.3 g of distillation condensate containing 16.9 g of ethyl pent-3-enoate, and 17.7 g of clear homogeneous red liquid residue containing:

(1) 44.3 mg (namely, 0.416 mg atom) of Pd;

(2) 16.12 g (namely, about 40 millimols) of Aliquat 336; and (3) 1.07 g of non-volatile organic products of high molecular weight, which are essentially ethyl nona-3,8-dienoate and C$_6$ diesters.

(8c) Recycling into the Carbonylation Autoclave

A carbonylation operation was carried out under conditions similar to those of step (8a), recycling the 17.68 g of the red distillation residue from step (8b) and using the amounts of starting materials indicated in Table IC.

47.66 g of a clear homogeneous green-yellow reaction mixture were recovered, the analysis of which is shown in Table IIA.

EXAMPLE 9

(9a) Carbonylation Step

A carbonylation operation was carried out under the conditions described in Example (1a), starting from:

(i) 0.1797 g (0.5 millimol, 1 mg atom of Pd) of bis-($\pi$-allyl-chloropalladium);

(ii) 8.85 g (30 millimols) of PBu$_4$+Cl$^-$, which corresponds to a molar ratio onium/Pd of 30;

(iii) 18.4 g (400 millimols) of ethanol;

(iv) 1.10 g (30 millimols) of HCl, which corresponds to a molar ratio HCl/Pd of 30; and (v) 27.2 g (400 millimols) of isoprene, which corresponds to a molar ratio diene/Pd of 400 and a molar ratio alcohol/diene of 1.

The said operation was carried out at 100° C. under 200 bars for 4 hours.

62.0 g of a homogeneous lemon-yellow solution were recovered, which contained:

(1) 9.4% by weight of ethanol (5.8 g); and (2) 54% by weight of $\beta,\gamma$-unsaturated esters (33.75 g) consisting of 94% of ethyl-4-methylpent-3-enoate and 6% of ethyl 3-methylpent-3-enoate and ethyl 2,3-dimethylbut-3-enoate.

The partial degree of conversion, RY, to $\beta,\gamma$-unsaturated esters was 59.4 mol %.

The specific activity A of the catalyst, expressed as ethyl 4-methylpent-3-enoate, was 56 hour$^{-1}$.

(9b) Distillation Step 29.8 g of the reaction mass from step (9a) were subjected to a distillation operation at a temperature of 90° C. and under an absolute pressure of 3,500 Pascals.

This provided:

(1) 18.0 g of distillation condensate containing 16 g of $\beta,\gamma$-unsaturated esters (namely, 88.8% by weight); and (2) 5.2 g of clear homogeneous red liquid distillation residue containing:

(2a) 4.25 g (14.4 millimols) of PBu$_4$Cl;

(2b) 51 mg (0.48 mg atom) of Pd; and (2c) 0.84 g of organic products.

(9c) Step of Recycling into the Carbonylation Autoclave

A carbonylation step was carried out under the conditions described under (9a), starting from:

(i) 5.2 g of the liquid distillation residue obtained in step (9b);

(ii) 9.2 g (200 millimols) of ethanol;

(iii) 526 mg (14.4 millimols) of HCl; and (iv) 13.1 g (192 millimols) of isoprene.

After a carbonylation time of 4 hours at 100° C. under 200 bars, 31.16 g of a clear homogeneous yellow solution were recovered, which contained 19.8 g (namely, 63% by weight) of $\beta,\gamma$-unsaturated esters containing 94% of ethyl 4-methylpent-3-enoate.

The partial degree of conversion, RY, to $\beta$, $\gamma$-unsaturated esters was 72.6 mol %.

The specific activity A of the catalyst, expressed as ethyl 4-methylpent-3-enoate, was 72 hour$^{-1}$.

(9d) Second Distillation Step 27 g of the reaction mass obtained in step (9c) were subjected to a distillation operation at a temperature of 82° C. and under 2,800 Pascals.

The following were collected:

(1) 19.1 g of distillation condensate containing 16.9 g (namely, 88.5% by weight) of $\beta,\gamma$-unsaturated esters; and (2) 5.8 g of homogeneous brown-red liquid distillation residue containing:

(2a) 3.7 g (12.5 millimols) of PBu$_4$Cl;
(2b) 44.2 mg (0.415 mg atom) of Pd; and
(2c) 2.0 g of organic products.

(9e) Extraction of the Products of High Molecular Weight 0.215 g of ethanol was added to the distillation residue from step (9d); this provided a viscous brown-red liquid, to which 8.8 g of n-dodecane were added at a temperature of 50° C.

The composition thus obtained contained:

(1) 1.5% by weight of ethanol, which corresponds to a weight ratio alkane/alcohol of 41; and (2) 25% by weight of PBu$_4$Cl, which corresponds to a molar ratio onium/Pd of 30 and a weight ratio onium/alcohol of 17.

After shaking, cooling to 10° C. and decantation, the medium separated into two phases:

(a) a colorless upper phase weighing 10.4 g and consisting of n-dodecane which has solubilized 1.6 g of organic products, and containing less than 3 ppm of Pd and less than 20 ppm of phosphorus, and (b) a very viscous, reddish-brown lower phase weighing 4.4 g and containing ethanol and more than 99.9% of the palladium and of the phosphonium salt.

The conditions and the results of this extraction step are summarized in Table IV.

The reddish-brown lower phase was recycled into the carbonylation autoclave for a further carbonylation operation.

EXAMPLE 10

(10a) Carbonylation Step

The following materials were introduced, under a stream of argon, into a 125 cm$^3$ autoclave made of nickel-molybdenum alloy marketed under the trademark HASTELLOY B2:

(i) 287.5 mg (namely, 0.5 millimol) of bis-(dibenzalacetone)-Pd;

(ii) 15.4 g (namely, 20 millimols) of tetradodecylammonium bromide, which corresponds to a molar ratio NDod$_4$Br/Pd of 40;

(iii) 12 g (namely, 261 millimols) of ethanol; and (iv) 2.7 g (namely, 20 millimols) of 1-bromobut-2-ene, which corresponds to a molar ratio HBr/Pd of 40.

The autoclave was closed; 13 g (namely, 241 millimols) of butadiene were transferred therein, which corresponds to a molar ratio butadiene/Pd of 482 and a molar ratio alcohol/butadiene of 1.08.

The autoclave, which was agitated by shaking, was heated to 10° C. and charged with CO at a constant total pressure of 145 bars.

The reaction was permitted to proceed for 1.5 hours at this temperature and then for 2 hours 10 minutes at 120° C. The autoclave was then cooled to 15° C. and degassed slowly.

30.8 g of a homogeneous orange solution, containing 18.5% by weight of ethanol and 15.6% by weight of ethyl pentenoates, were recovered.

Table V reports the results of gas chromatographic analysis of the solution obtained, together with the S and the RY corresponding to each product formed.

The overall degree of conversion of the butadiene, DC, was 25 mol %.

The specific activity A of the catalyst was 19 hour$^{-1}$.

(10b) Distillation Step (Summarized in Table IIIC)

The 30.8 g of the clear homogeneous orange solution obtained in carbonylation step (10a) were subjected to a distillation operation at a temperature of 93° C. and under a pressure of about 3,500 Pascals. This provided:

(1) 11.7 g of distillation condensate containing 2.96 g of pentenoic acid esters; and (2) 16.6 g of homogeneous, bright red liquid residue containing 0.5 mg atom of Pd, 20 millimols of tetradodecylammonium bromide and 0.9 g of the nonvolatile organic products consisting of nona-3,8-dienoate and C$_6$ diesters.

(10c) Recycling into the Carbonylation Autoclave

A carbonylation step was carried out under the conditions described in step (10a), using the 16.6 g of dark red liquid residue obtained in distillation step (10b) and the following amounts of reactants:

(i) 2.7 g (namely, 20 millimols) of 1-bromobut-2-ene;
(ii) 12 g (namely, 261 millimols) of ethanol; and
(iii) 13.5 g (namely, 250 millimols) of butadiene, which corresponds to a molar ratio butadiene/palladium of 500 and a molar ratio alcohol/butadiene of 1.04.

The operation was carried out for 1 hour at 100° C. for 3 hours at 120° C., CO being charged therein at a constant total pressure of 145 bars.

34.6 g of a homogeneous orange solution, containing 20.3% by weight of ethanol and 15.5% by weight of ethyl pentenoates, were recovered.

Table V reports the results of gas chromatographic analysis of the solution obtained, together with the S and RY corresponding to each product formed.

The overall degree of conversion of the butadiene, DC, was 25.5 mol %, the specific activity A of the catalyst was 21 hour$^{-1}$.

EXAMPLE 11

(11a) Carbonylation Step

The following materials were introduced, under a stream of argon, into a 125 cm$^3$ autoclave made of nickel-molybdenum alloy marketed under the trademark HASTELLOY B2:

(i) 75 mg (namely, 0.423 millimol) of PdCl$_2$;
(ii) 12.46 g (42.3 millimols) of PBu$_4^+$Cl$^-$, which corresponds to a ratio PBu$_4$Cl/Pd of 100;
(iii) 12 g (261 millimols) of ethanol; and
(iv) 1.912 g (21.2 millimols) of 1-chlorobut-2-ene, which corresponds to a molar ratio HCl/Pd of 50.

The autoclave was closed; 13.5 g (250 millimols) of butadiene were transferred therein, which corresponds to a molar ratio butadiene/Pd of 591 and a molar ratio alcohol/butadiene of 1.04.

The autoclave was heated to 120° C. and charged with CO at a constant total pressure of 145 bars.

The reaction was permitted to proceed for 4 hours and the autoclave was then cooled and degassed.

The reaction conditions are summarized in Table 1D.

43.4 g of a homogeneous, light green solution were recovered, the analysis of which is reported in Table IIB.

The overall degree of conversion of the butadiene, DC, was 83.6 mol %.

The specific activity A of the catalyst was 110 hour$^{-1}$.

(11b) Distillation Step (Summarized in Table IIIC)

42.24 g of the reaction mass obtained in carbonylation step (11a) were subjected to a distillation operation at 80° C. under 3,500 Pa.

The following were collected:

(1) 23.8 g of distillation condensate containing 22.6 g of ethyl pentenoates; and (2) 15.1 g of clear homogeneous red liquid residue containing:

(2a) 41.2 millimols of PBu$_4$Cl;
(2b) 0.41 mg atom of Pd;
(2c) 0.32 g of ethyl nona-3,8-dienoate; and
(2d) 2.01 g of C$_6$ diesters.

(11c) Extraction of the Products of High Molecular Weight (Summarized in Table IV)

The following materials were added to the distillation residue from step (11b):

(1) 3 g of water; and (2) 36.2 g of n-dodecane, which corresponds to a weight ratio PBu$_4$$^+$Cl$^-$/water of 4.04 and a weight ratio dodecane/water of 12.

The medium separated into two phases:

(a) a colorless upper phase (37.7 g) containing the dodecane and about 62% of the ethyl nona-3,8-dienoate and 67% of the C$_6$ diesters, less than 5.5 ppm of Pd and less than 23 ppm of P; and (b) a red lower phase (16.2 g) containing the water, more than 99.4% of the Pd catalyst and more than 99.9% of the PBu$_4$Cl.

(11d) Removal of the Water

The red lower phase was heated to 90° C. under 3,500 Pa, until all of the water has been removed.

13.2 g of a residue containing 0.411 mg atom of Pd and 41.1 millimols of the onium were collected, which were recycled in the molten state into the carbonylation autoclave.

(11e) Carbonylation

A carbonylation step was carried out under the conditions indicated in step (11a), using the 13.2 g of residue and the following amounts of reactants:

(i) 1.86 g (namely, 20.55 millimols) of 1-chlorobut-2-ene;
(ii) 12 g (namely, 261 millimols) of ethanol; and
(iii) 13.5 g (namely, 250 millimols) of butadiene, which corresponds to the following molar ratios: HCl/Pd=50, butadiene/Pd=608, alcohol/butadine=104.

The operation was carried out at 120° C. for 2 hours, CO being charged therein at a constant total pressure of 145 bars.

42.8 g of a homogeneous green solution, containing 3.1% by weight of ethanol and 49.4% by weight of ethyl pentenoates, were recovered.

The result of the gas chromatographic analysis is reported in Table II B.

The overall degree of conversion of the butadiene, DC, was 72.9 mol % and the specific activity A of the catalyst was 201 hour$^{-1}$.

EXAMPLE 12

(12a) Carbonylation Step

This step was described in Example (4e); the reaction mass obtained weighed 67.2 g and was in the form of a homogeneous green solution.

(12b) Distillation Step (Summarized in Table IIIC)

62.9 g of this reaction mass were taken and 16.52 g of PBu$_4$Cl and 98.8 mg of PdCl$_2$ were added thereto.

The composition obtained contained 1.077 mg atoms of Pd and 108.3 millimols of PBu$_4$Cl.

This composition was subjected to a distillation operation at 82° C. under about 3,500 Pa.

The following were collected:

(1) 33.7 g of distillation condensate containing 26.2 g of ethyl pentenoates; and (2) 42.10 g of a homogeneous orange-brown liquid residue containing:

(2a) 1.077 mg atom of Pd;
(2b) 108.3 millimols of PBu$_4$Cl;
(2c) 0.83 g of ethyl nonadienoate; and (2d) 3.75 g of C$_6$ diesters.

(12c) Extraction of the Products of High Molecular Weight (Summarized in Table IV)

9 g of orange-brown residue were taken (which corresponds to 0.230 mg atom of Pd and 23.15 millimols of PBu$_4$Cl) and 13 g of acetonitrile and 40 g of n-octane were added thereto, which corresponds to:

(a) a weight ratio onium/polar solvent of 0.53; (b) a weight ratio n-octane/polar solvent of 3.1; and (c) a molar ratio onium/Pd of 100.

The medium separated into two phases:

(a) a colorless upper phase weighing 39.8 g and containing the n-octane, more than 60% of the organic products of high molecular weight, less than 1.5 ppm of Pd and less than 30 ppm of P, and (b) an orange lower phase weighing 21.4 g and containing the acetonitrile, more than 99.7% of the Pd and more than 99.8% of the onium.

(12d) Removal of the Acetonitrile.

The orange lower phase was subjected to a distillation operation at 70° C. under 3,500 Pa, until all of the acetonitrile has been removed.

A viscous homogeneous orange-brown liquid containing 0.230 mg atom of Pd and 23.1 millimols of PBu$_4$Cl was recovered, which was recycled in the molten state into the carbonylation autoclave.

(12e) Carbonylation Step

The following materials were also introduced into the carbonylation autoclave:

(i) 7 g (namely, 152 millimols) of ethanol;
(ii) 1.04 g (namely 11.5 millimols) of 1-chlorobut-2-ene; and
(iii) 10 g (namely, 185 millimols of butadiene, which corresponds to the following molar ratios: HCl/Pd=50, butadiene/Pd=805, alcohol/butadiene=0.82.

The carbonylation operation was carried out for 2 hours at 120° C., CO being charged therein at a constant total pressure of 145 bars. The reaction conditions are summarized in Table 1D.

This provided 27.8 g of a homogeneous green solution, the analysis of which is reported in Table II B.

The overall degree of conversion of the butadiene, DC, was 56.4 mol %. The specific activity of the catalyst, A, was 206 hour$^{-1}$.

EXAMPLE 13

(13a) Extraction of the Products of High Molecular Weight (Summarized in Table IV)

21.5 g of the distillation residue obtained in Example (12b) were taken, which corresponds to 0.55 mg atom of Pd and 55.4 millimols of PBu$_4$Cl.

27 g of N,N-dimethylformamide and 81 g of cyclohexane were added thereto, which corresponds to:
 (a) a weight ratio onium/polar solvent of 0.61;
 (b) a weight ratio apolar solvent/polar solvent of 3; and
 (c) a molar ratio onium/Pd of 100.

The medium separated into two phases:
 (a) a colorless upper phase weighing 86.8 g and containing the cyclohexane, more than 80% of the organic products of high molecular weight, less than 3 ppm of Pd and less than 65 ppm of P; and
 (b) a brown lower phase weighing 48.4 g and containing the dimethylformamide, more than 99.5% of the Pd and more than 99.5% of the onium.

(13b) Removal of the N,N-dimethylformamide

The brown lower phase was subjected to a distillation operation at 80° C. under about 3,500 Pa, until all of the dimethylformamide has been removed.

18.20 g of a homogeneous, light brown residue consisting of 0.55 mg atom of Pd and 55.4 millimols of PBu$_4$Cl were recovered, which were recycled in the molten state into the carbonylation autoclave.

(13c) Carbonylation Step

The following were also introduced into the carbonylation autoclave:
 (i) 12 g (namely, 261 millimols) of ethanol;
 (ii) 2.49 g (namely, 27.5 millimols) of 1-chlorobut-2-ene; and
 (iii) 14 g (namely, 259 millimols) of butadiene, which corresponds to the following molar ratios: HCl/Pd=50, butadiene/Pd=470 and alcohol/butadiene=about 1.

The carbonylation operation was carried out for 2 hours at 120° C., CO being charged therein at a constant total pressure of 145 bars. The carbonylation conditions are summarized in Table I D. 50.4 g of a homogeneous green reaction mass were recovered, the analysis of which is reported in Table II B.

The overall degree of conversion of the butadiene, DC, was 76.5%. The specific activity A of the catalyst was 165 hour$^{-1}$.

EXAMPLE 14

Comparative Example with NBu$_4$Cl

This example is given by way of comparison, using infusible quaternary ammonium chloride (decomposition about 200° C.) as the quaternary onium salt.

(14a) Carbonylation Step

A carbonylation operation was carried out under the conditions described in Example 1a, starting from:
 (i) 14.5 g (268.5 millimols) of butadiene;
 (ii) 0.0750 g (0.423 millimols) of PdCl$_2$;
 (iii) 12 g (261 millimols) of ethanol;
 (iv) 1.914 g (21.15 millimols) of 1-chlorobut-2-ene; and
 (v) 11.75 g (42.25 millimols) of NBu$_4$Cl.

The said operation was carried out at 120° C. and under a pressure of 145 bars for 2 hours.

44 g of a homogeneous green solution containing 48% of ethyl pent-3-enoate were recovered, which corresponds to a specific activity of 195 hour$^{-1}$.

(14b) Distillation Step 36.2 g of the reaction mass were subjected to a distillation operation at a temperature of 80° C. and under an absolute pressure of 3,500 Pascals.

It was found that the turbid brown distillation residue was not a homogeneous liquid, but solidified and crystallized on the walls of the distillation apparatus; the said residue therefore cannot be directly recycled.

Example 15

This example is also given by way of comparison, the fusible quaternary onium chloride being replaced, in the distillation step, by an organic solvent which was non-volatile under the conditions of the distillation operation.

(15a) Carbonylation Step

The carbonylation step described in Example (6a) was carried out under identical conditions.

The results of the carbonylation reaction were identical.

(15b) Distillation Step 24.2 g of diethyl 2-methylglutarate were added to the reaction mass obtained (53 g).

A distillation operation was carried out at a temperature of 90° C. and under an absolute pressure of 3,700 Pascals.

It was found that the dark brown distillation residue obtained was turbid and contained solid palladium metal in suspension, which cannot easily be recycled on an industrial scale.

Moreover, in contrast to the process forming the subject of the present invention, the separation of the products of high molecular weight from the palladium catalyst cannot be carried out in a simple and efficient manner, which makes any industrial application hazardous because of the progressive accumulation of the products of high molecular weight which cannot be separated off.

TABLE I

| Ex | BD milli- mols | ROH milli- mols | Catalyst mg atom of Pd | Co-catalyst Millimoles | BD/ Pd in mols | HCl/ Pd in mols | Onium Milli- mols | Onium/Pd in mols | T °C. | Time hours | PCO bars | RM weight g | color |
| --- | --- | --- | --- | --- | --- | --- | --- | --- | --- | --- | --- | --- | --- |

TABLE I-continued

| Ex | diene milli-mols | ROH milli-mols | Catalyst mg atom of Pd | | Co-catalyst millimoles | | diene/Pd | HCl/Pd | Onium milli-mols | Onium/Pd | T °C. | Time hours | PCO bars | RM weight g | color |
|---|---|---|---|---|---|---|---|---|---|---|---|---|---|---|---|
| | | EtOH | [<(PdCl]$_2$ | | ⌐⌐⌐Cl (allyl) | | | | PBu$_4$Cl | | | | | | |
| 1a | 269 | 261 | 0.423 | | 2.1 | | 636 | 5 | 42.2 | 100 | 120 | 2 | 196 | 41.17 | yellow-green |
| 1c | 111 | 130 | 0.206 | | 1.03 | | 540 | 5 | 20.5 | 100 | 120 | 2 | 196 | 19.02 | yellow-green |
| | | | PdCl$_2$ | | HCl | | | | | | | | | | |
| 2a | 426 | 522 | 0.845 | | 42.2 | | 500 | 50 | 0 | 0 | 120 | 2 | 145 | 46.6 | yellow |
| | | | | | ⌐⌐⌐Cl | | | | | | | | | | |
| 2c | 259 | 261 | 0.356 | | 21.1 | | 728 | 60 | 10.17 | 28 | 120 | 2 | 145 | 27.3 | green |
| 2c | 296 | 261 | 0.356 | | 21.1 | | 830 | 60 | 20.34 | 56 | 120 | 2 | 145 | 33.7 | green |
| 2g | 296 | 261 | 0.356 | | 21.1 | | 830 | 60 | 20.34 | 56 | 120 | 2 | 145 | 33.3 | green |
| 2j | 278 | 261 | 0.355 | | 21.1 | | 780 | 60 | 20.24 | 56 | 120 | 2 | 145 | 32.5 | green |
| | | EtOH | Pd(DBA)$_2$ | | ⌐⌐⌐Cl | | | | PBu$_4$Cl | | | | | | |
| 3a | 426 | 500 | 3.0 | | 60 | | 142 | 20 | 23.9 | 8 | 120 | 2 | 120 | 53.9 | red |
| 3c | 426 | 500 | 2.87 | | 60 | | 148 | 20 | 23 | 8 | 120 | 2 | 120 | 46.35 | red |
| | | | PdCl$_2$ | | | | | | | | | | | | |
| 4a | 398 | 400 | 0.60 | | 30 | | 713 | 50 | 15 | 25 | 120 | 4.5 | 130 | 53.1 | light green |
| 4c | 370 | 400 | 0.571 | | 30 | | 650 | 52.6 | 14.3 | 25 | 120 | 2 | 145 | 40.61 | green |
| 4e | 361 | 400 | 0.56 | | 30 | | 645 | 53.5 | 13.39+42.07 | 100 | 120 | 2 | 145 | 67.2 | green |
| 5a | 278 | 261 | 0.217 | | 10.5 | | 1313 | 50 | 42.2 | 200 | 140 | 1.37 | 145 | 47.8 | green |
| 5c | 278 | 261 | 0.184 | | 10.5 | | 1510 | 56 | 38 | 200 | 140 | 1 | 145 | 39.8 | green |

| Ex | diene milli-mols | ROH milli-mols | Catalyst mg atom of Pd | Co-catalyst millimoles | diene/Pd | HCl/Pd | Onium milli-mols | Onium/Pd | T °C. | Time hours | PCO bars | RM weight g | color |
|---|---|---|---|---|---|---|---|---|---|---|---|---|---|
| | BD | MeOH | PdCl$_2$ | ⌐⌐⌐Cl | | | PBu$_4$C | | | | | | |
| 6a | 259 | 250 | 1.268 | 42.2 | 205 | 33 | 42.2 | 33 | 100 | 2 | 120 | 33 | green |
| 6c | 268 | 250 | 1.222 | 40.3 | 220 | 33 | 40.7 | 33 | 100 | 2 | 120 | 30.3 | green |
| | | EtOH | | HCl | | | | | | | | | |
| 7a | 444 | 522 | 0.845 | 42.2 | 525 | 50 | 0 | 0 | 120 | 2 | 145 | 52.6 | yellow |
| | | | | ⌐⌐⌐Cl | | | Aliquat | | | | | | |
| 8a | 259 | 261 | 0.423 | 21.1 | 612 | 50 | 40.6 | 96 | 120 | 2 | 145 | 47.5 | yellow |
| 8c | 268 | 261 | 0.416 | 21.1 | 644 | 50 | 40 | 96 | 120 | 2 | 145 | 47.5 | yellow |
| | isobutene | | [<(PdCl]$_2$ | HCl | | | PBu$_4$Cl | | | | | | |
| 9a | 400 | 400 | 1.0 | 30 | 400 | 30 | 30 | 30 | 100 | 4 | 200 | 62.0 | lemon-yellow |
| 9c | 192 | 200 | 0.48 | 14.4 | 400 | 30 | 14.4 | 30 | 100 | 4 | 200 | 31.2 | yellow-green |
| | BD | EtOH | PdCl$_2$ | ⌐⌐⌐Cl | | | PBu$_4$Cl | | | | | | |
| 11a | 250 | 261 | 0.423 | 21.1 | 591 | 50 | 42.3 | 100 | 120 | 4 | 145 | 43.4 | green |
| 11e | 250 | 261 | 0.411 | 20.55 | 608 | 50 | 41.1 | 100 | 120 | 2 | 145 | 42.8 | green |
| 12e | 185 | 152 | 0.230 | 11.5 | 805 | 50 | 23.1 | 100 | 120 | 2 | 145 | 27.8 | green |
| 13c | 259 | 261 | 0.55 | 27.5 | 470 | 50 | 55.4 | 100 | 120 | 2 | 145 | 50.4 | green |

TABLE II

| Ex | DC % | A hour$^{-1}$ | P$_3$ + P$_4$ S % | P$_3$ + P$_4$ RY % | P' S % | P' RY % | C$_9$ S % | C$_9$ RY % | HC$_8$ S % | HC$_8$ RY % | ROC$_4$ S % | ROC$_4$ RY % | C$_6$ S % | C$_6$ RY % | RYCl % | Residual ROH g |
|---|---|---|---|---|---|---|---|---|---|---|---|---|---|---|---|---|
| 1a | 80.7 | 232 | 90.8 | 73.3 | 1.9 | 1.5 | 1.4 | 1.1 | 0.7 | 0.6 | ε | ε | 2.0 | 1.6 | 0.8 | 2.15 |
| 1c | 86.5 | 221 | 94.5 | 81.7 | 1.7 | 1.4 | 0.3 | 0.3 | 0.2 | 0.2 | ε | ε | 2.4 | 2.1 | 0.4 | 0.9 |
| 2a | 53.9 | 121 | 90 | 48.5 | 2.9 | 1.6 | 1.2 | 0.7 | 2.1 | 1.3 | 1.8 | 0.9 | 1.0 | 0.6 | 1.6 | 13.1 |
| 3a | 42.4 | 22.4 | 83.7 | 35.5 | 2.0 | 0.8 | 2.4 | 1 | 4.8 | 2 | 1 | 0.4 | 0.1 | 0.4 | 6.4 | 12.5 |
| 3c | 26.1 | 15.8 | 81.2 | 21.3 | 2.2 | 0.6 | 1.7 | 0.4 | 9.3 | 2.4 | 0.4 | 0.1 | 1.2 | 0.3 | 3.9 | 13.5 |
| 4a | 70.5 | 85 | 81.6 | 57.5 | 1.6 | 1.1 | 7.3 | 5.2 | 3.8 | 2.7 | ε | ε | 3.1 | 2.2 | 4.6 | 4.44 |
| 4c | 40.2 | 112 | 85.5 | 31.8 | 2.2 | 0.8 | 3.6 | 1.5 | 3.8 | 1.4 | ε | ε | 3.6 | 1.5 | 3.3 | 10.97 |
| 4e | 74.9 | 220 | 91.0 | 68.2 | 1.9 | 1.4 | 1.1 | 0.8 | 2.0 | 1.5 | ε | ε | 2.7 | 2.0 | 3.7 | 4.99 |
| 5a | 73.1 | 608 | 88.7 | 64.9 | 1.8 | 1.3 | 2.6 | 1.9 | 2.2 | 1.6 | ε | ε | 2.9 | 2.1 | 6.0 | 2.4 |
| 5c | 42.3 | 570 | 87.2 | 36.9 | 2.7 | 2.3 | 1.6 | 0.7 | 7 | 3 | ε | ε | 1 | 0.4 | 2.6 | 6.5 |
| 6a | 45.5 | 44 | 93.9 | 42.7 | 1.5 | 0.7 | 0.9 | 0.4 | 2.7 | 1.2 | ε | ε | 0.6 | 0.2 | | 5.1 |
| 6c | 39.6 | 40 | 92.0 | 36.4 | 1.8 | 0.7 | 1.3 | 0.5 | 2.5 | 1.0 | 0.3 | 0.1 | 0.8 | 0.3 | | 4.7 |

TABLE II-continued

| Ex | DC % | A hour$^{-1}$ | P$_3$ + P$_4$ S % | P$_3$ + P$_4$ RY % | P' S % | P' RY % | C$_9$ S % | C$_9$ RY % | HC$_8$ S % | HC$_8$ RY % | ROC$_4$ S % | ROC$_4$ RY % | C$_6$ S % | C$_6$ RY % | RYCl % | Residual ROH g |
|---|---|---|---|---|---|---|---|---|---|---|---|---|---|---|---|---|
| 7a | 54.3 | 132 | 92.0 | 50 | 2.2 | 1.2 | 1.3 | 0.7 | 2.8 | 1.5 | 1.4 | 0.8 | 0.2 | 0.1 | 3.2 | 12.6 |
| 8a | 58.9 | 163 | 90.1 | 53.1 | 1.5 | 0.9 | 1.5 | 0.9 | 2.2 | 1.3 | ε | ε | 2.9 | 1.7 | 5.9 | 4.3 |
| 8c | 55.5 | 157 | 87.2 | 48.7 | 1.6 | 0.9 | 3.5 | 2 | 2.3 | 1.3 | ε | ε | 2.8 | 1.6 | 6.1 | 4.2 |
| 11a | 83.6 | 110 | 88.8 | 74.2 | 1.2 | 1.0 | 1.8 | 1.5 | 0.6 | 0.5 | ε | ε | 5.3 | 4.4 | 3.0 | 0.04 |
| 11e | 72.9 | 201 | 90.6 | 66.1 | 1.5 | 1.2 | 0.9 | 0.7 | 0.9 | 0.7 | ε | ε | 3.8 | 2.8 | 3.6 | 1.33 |
| 12e | 56.4 | 206 | 91.1 | 51.3 | 1.9 | 1.1 | 1.2 | 0.7 | 0.8 | 0.5 | ε | ε | 3.0 | 1.7 | 2.6 | 0.73 |
| 13c | 76.5 | 165 | 91.4 | 69.9 | 1.5 | 1.1 | 1.2 | 0.9 | 1.0 | 0.8 | ε | ε | 1.6 | 1.2 | 2.8 | 0.8 |

TABLE III

| Ex | RM g | PBu$_4$Cl milli-mols | Onium/Pd in mols | T °C. | P Pa | Distillation residue g | Distillation residue color | Distillation residue Pd mg atoms | Distillation residue Onium milli-mols | Distillation residue Organic products g | Condensate g | Condensate P$_3$ + P$_4$ g |
|---|---|---|---|---|---|---|---|---|---|---|---|---|
| 1b | 20 | 20.5 | 100 | 84 | 3500 | 7.5 | orange | 0.206 | 20.5 | 1.5 | 10.8 | 10.3 |
| 1d | 15.1 | 15.4 | 100 | 84 | 3100 | 4.95 | orange | 0.155 | 15.4 | 0.4 | 8.4 | |
| 2b | 19.6 | 10.2 | 28 | 85 | 3500 | 3.69 | red | 0.356 | 10.3 | 0.6 | 11.3 | 9.7 |
| 2d | 27.3 | 10.17 × 2 | 56 | 80 | 3500 | 7.29 | orange | 0.356 | 20.3 | 1.23 | 13.7 | 7.7 |
| 2f | 33.7 | 20.3 | 56 | 83 | 3500 | 8.2 | | 0.356 | 20.3 | 2.14 | 20.3 | 10.2 |
| 2h | 33.3 | 20.3 | 56 | 82 | 3500 | 8.5 | | 0.356 | 20.3 | 2.4 | 21.2 | 10.7 |
| 2k | 32.5 | 20.2 | 56 | 82 | 3500 | 7.2 | green | 0.355 | 20.2 | 1.1 | 18.7 | 9.6 |
| 3b | 51.6 | 23 | 8 | 76 | 3500 | 10.25 | red | 2.87 | 23 | 1.8 | 28.4 | 16.2 |
| 4b | 50.6 | 14.3 | 25 | 86 | 3500 | 7.4 | | 0.571 | 14.3 | 3.0 | 28.7 | 26.7 |
| 4d | 39.6 | 14 | 25 | 80 | 3500 | 8.4 | | 0.56 | 14 | 4.2 | 18.8 | 16.2 |

| Ex | RM g | Onium milli-mols | Onium/Pd in mols | T °C. | P Pa | Distillation residue g | Distillation residue color | Distillation residue Pd mg atoms | Distillation residue Onium milli-mols | Distillation residue Organic products g | Condensate g | Condensate P$_3$ + P$_4$ g |
|---|---|---|---|---|---|---|---|---|---|---|---|---|
| | | PBu$_4$Cl | | | | | | | | | | |
| 5b | 40.7 | 38 | 200 | 76 | 3500 | 14.5 | yellow-orange | 0.184 | 38 | 3.8 | 22.7 | 19.5 |
| 5d | 39.2 | 37.5 | 200 | 80 | 3500 | 13.9 | yellow-orange | 0.184 | 37.5 | 2.5 | 22.2 | |
| 6b | 33 | 42.2 | 33 | 85 | 4700 | 13.0 | orange | 1.268 | 42.2 | 0.3 | 16.9 | 12.3 |
| 7b | 17 | 27.4 | 100 | 76 | 3500 | 8.55 | dark yellow | 0.276 | 27.4 | 0.4 | 10.3 | 9.1 |
| | | Aliquat | | | | | | | | | | |
| 8b | 46.7 | 40 | 96 | 74 | 3500 | 17.7 | red | 0.416 | 40 | 1.1 | 22.3 | 16.9 |
| | | PBu$_4$Cl | | | | | | | | | | |
| 9b | 29.8 | 14.4 | 30 | 90 | 3500 | 5.2 | red | 0.48 | 14.4 | 0.84 | 18.0 | 16.0 |
| 9d | 27.0 | 12.5 | 30 | 82 | 2800 | 5.8 | red-brown | 0.42 | 12.5 | 2.0 | 19.1 | 16.9 |
| | | NDod$_4$Br | | | | | | | | | | |
| 10b | 30.8 | 20 | 40 | 93 | 3500 | 16.6 | red | 0.5 | 20 | 0.9 | 11.7 | 2.96 |
| | | PBu$_4$Cl | | | | | | | | | | |
| 11b | 42.24 | 41.2 | 100 | 80 | 3500 | 15.1 | red | 0.41 | 41.2 | 2.33 | 23.8 | 22.6 |
| 12b | 62.9 | 108.3 | 100 | 82 | 3500 | 42.1 | orange | 1.077 | 108.3 | 4.58 | 33.7 | 26.2 |

TABLE IV

| Ex | Onium/Pd in mols | Alkane in g | Polar in g | Alkane polar by weight | Onium polar by weight | g | Polar phase % recovered of Pd | Polar phase % recovered of onium | g | Alkane phase % recovered of C$_9$ + C$_6$ | Pd ppm |
|---|---|---|---|---|---|---|---|---|---|---|---|
| 1e | 100 | n-hexane 40 | MeOH 13 | 3,1 | 0.35 | 16.8 | >99.4 | >99.4 | 41.1 | | <4 |
| 2i | 56 | n-octane 33.4 | EtOH 4.4 | 7.6 | 1.4 | 12.6 | >99.6 | >99.5 | 33.7 | | <7 |

TABLE IV-continued

| Ex | Onium/Pd in mols | Alkane in g | Polar in g | Alkane polar by weight | Onium polar by weight | Polar phase % recovered of | | Alkane phase % recovered of | | Pd ppm |
|---|---|---|---|---|---|---|---|---|---|---|
| | | | | | | g | Pd | onium | g | $C_9 + C_6$ | |
| 5e | 200 | isooctane 15 | EtOH 3.6 | 4.2 | 2.9 | 14.5 | >99.8 | >99.8 | 17.9 | >80 | <2.5 |
| 9e | 30 | n-dodecane 8.8 | EtOH 0.215 | 41 | 17 | 4.4 | >99.9 | >99.9 | 10.4 | >90 | <3 |
| 11c | 100 | n-dodecane 36.2 | water 3 | 12 | 4.04 | 16.26 | >99.4 | >99.9 | 37.7 | >65 | <5.5 |
| 12c | 100 | n-octane 40 | AN 13 | 3.1 | 0.53 | 21.4 | >99.7 | >99.8 | 39.8 | >60 | <1.5 |
| 13a | 100 | cyclohexane 81 | DMF 27 | 3 | 0.61 | 48.4 | >99.5 | >99.5 | 86.8 | >80 | <3 |

TABLE V

| Ex | DC % | A hour$^{-1}$ | $P_3 + P_4$ | | P' | | $C_9$ | | $H_8$ | | $ROC_4$ | | $C_6$ | | RYBr % |
|---|---|---|---|---|---|---|---|---|---|---|---|---|---|---|---|
| | | | S % | RY % | S % | RY % | S % | RY % | S % | RY % | S % | RY % | S % | RY % | |
| 10a | 25 | 19 | 62.4 | 15.6 | 1.0 | 0.2 | 2.3 | 0.6 | 11.9 | 3.0 | 9.1 | 2.3 | 3.2 | 0.8 | 2.5 |
| 10c | 25.5 | 21 | 66 | 16.8 | 0.9 | 0.2 | 3.5 | 0.9 | 10.9 | 2.8 | 5.2 | 1.3 | 4.1 | 1.0 | 2 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an ester of a $\beta,\gamma$-unsaturated carboxylic acid, comprising (i) carbonylating a conjugated diene with carbon monoxide in the presence of an alcohol, a halogenated hydracid and a palladium catalyst; (ii) distilling the carbonylation reaction product in the presence of an ammonium, phosphonium or arsonium quaternary onium chloride or bromide having a melting point below the temperature at which the carbonylation reaction is carried out, and at a temperature and pressure such that said reaction product separates into a gaseous phase and a homogeneous liquid phase; (iii) recovering said gaseous phase comprising the ester of the $\beta,\gamma$-unsaturated carboxylic acid corresponding to the reactant diene and alcohol, an unreacted diene and alcohol, and any volatile reaction products of low molecular weight; (iv) recovering said homogeneous liquid phase comprising a mixture of the quaternary onium chloride or bromide and the palladium catalyst, and any non-volatile reaction products of high molecular weight; and (v) recycling the homogeneous liquid phase comprising said mixture of quaternary onium chloride or bromide and the palladium cadalyst, into carbonylation reaction medium.

2. The process as defined by claim 1, said recycling (v) being after removing any reaction products of high molecular weight from said homogeneous liquid phase.

3. The process as defined by claim 1, wherein the quaternary onium chloride or bromide is one of the following salts: tetrabutylphosphonium chloride, methyl-tri-(octyl, nonyl or decyl)-ammonium chlorides or their mixtures, methyltributylammonium chloride, benzylbutyldimethylammonium chloride, benzylhexadecyldimethylammonium chloride, benyzldimethyltetradecylammonium chloride, hexadecyltributyl-phosphonium bromide, tetrabutylammonium bromide, tetradodecylammonium bromide, tetraheptylammonium bromide, tetrahexylammonium bromide, tetradecylammonium bromide, tetraoctadecylammonium bromide, tetraoctylammonium bromide, tetrapentylammonium bromide, tributylheptylammonium bromide and tributylpentylammonium bromide.

4. The process as defined by any of claims 1, 2 or 3, wherein the amount of quaternary onium chloride or bromide present for carrying out the distillation step (ii) corresponds to a molar ratio quaternary onium cation/palladium of at least 2.

5. The process as defined by claim 4, wherein said molar ratio quaternary onium cation/palladium ranges from 5 to 250.

6. The process as defined by claim 4, wherein the quaternary onium chloride or bromide present during the distillation step (ii) is introduced into the carbonylation reaction medium, either in total after a first carbonylation reaction, or in fractions over the course of a series of carbonylation/distillation steps (i) and (ii).

7. The process as defined by claim 4, wherein all or a portion of the quaternary onium chloride or bromide present during the distillation step (ii) is employed in the carbonylation reaction medium.

8. The process as defined by claim 1, further comprising removing said non-volatile reaction products of high molecular weight by (1) contacting said homogeneous liquid phase which comprises admixture of quaternary onium chloride or bromide and palladium catalyst, and said non-volatile reaction products of high molecular weight, with an apolar aliphatic or cycloaliphatic hydrocarbon solvent, a polar solvent which is immiscible with said apolar solvent; (2) decanting the polar phase and the apolar phase which result from said contacting step (i); (3) separating the apolar phase containing the reaction products of high molecular weight to be recovered from the polar phase containing the mixture of quaternary onium chloride or bromide and palladium catalyst; and (4) recycling said mixture of quaternary onium chloride or bromide and palladium catalyst, either in the form of an alcoholic solution thereof, or in the molten state after removal of the polar solvent, into the carbonylation reaction medium, said contacting step (i) being carried out utilizing an amount of quaternary onium chloride or bromide corresponding to a molar ratio quaternary onium cation/palladium of at least 20, and amounts of polar solvent and apolar hydrocarbon solvent which are at least equal to those necessary for the decantation of the contacting medium to form a polar phase and an apolar phase.

9. The process as defined by claim 8, wherein said contacting step (1) is carried out in the presence of an amount of polar solvent corresponding to a weight ratio quaternary onium chloride or bromide/polar solvent of at least 0.1 and an amount of apolar hydrocarbon solvent corresponding to a weight ratio apolar hydrocarbon solvent/polar solvent of more than 1.

10. The process as defined by claims 8 or 9, wherein said contacting step (1) is carried out in the presence of an amount of quaternary onium salt corresponding to a molar ratio onium cation/palladium ranging from 20 to 300, an amount of polar solvent corresponding to a weight ratio quaternary onium salt/polar solvent ranging from 0.25 to 30, and an amount of apolar solvent corresponding to a weight ratio apolar solvent/polar solvent of more than 2.

11. The process as defined by claim 10, wherein said polar solvent has a dielectric constant of more than 20.

12. The process as defined by claim 11, wherein said polar solvent has a dielectric constant of more than 30.

13. The process as defined by claim 8, wherein said polar solvent is water, acetonitrile, N,N-dimethylformamide, dimethyl sulfoxide, nitromethane or N-methylpyrrolidone.

14. The process as defined by claim 8, wherein said polar solvent is a linear or branched chain aliphatic monoalcohol having from 1 to 4 carbon atoms.

15. The process as defined by claim 14, wherein said polar solvent is a linear or branched chain aliphatic monoalcohol having from 1 to 3 carbon atoms.

16. The process as defined by claim 8, wherein said apolar solvent has a dielectric constant of less than 2.3.

17. The process as defined by claim 16, wherein said apolar solvent has a dielectric constant of less than 2.1.

18. The process as defined by claim 17, wherein said apolar solvent is pentane, isopentane, hexane, cyclohexane, octane, cyclooctane, 2,2,4-trimethylpentane, decane, dodecane, tetradecane, hexadecane or admixtures thereof of petroleum ether type.

19. The process as defined by claim 1, further comprising removing said non-volatile reaction products of high molecular weight by (1) contacting the constituents of the homogeneous liquid phase, separated during the distillation (ii) with an apolar aliphatic or cycloaliphatic hydrocarbon solvent at a temperature which is below or equal to the temperature of solidification of the homogeneous liquid phase; (2) filtering the solid/liquid system which results; (3) removing the solution of non-volatile reaction products of high molecular weight in said apolar solvent; (4) converting the resdiue of filtration, comprising a mixture of quaternary onium chloride or bromide and palladium cadalyst, to a homogeneous liquid either by melting or by dissolution in an alcohol; and (5) recycling said resultant homogeneous liquid into the carbonylation reaction medium.

20. The process as defined by claim 19, wherein said apolar solvent has a dielectric constant of less than 2.3.

21. The process as defined by claim 20, wherein said apolar solvent has a dielectric constant of less than 2.1.

22. The process as defined by claim 21, wherein said apolar solvent is pentane, isopentane, hexane, cyclohexane, octane, cyclooctane, 2,2,4-trimethylpentane, decane, dodecane, tetradecane, hexadecane or admixtures thereof of petroleum ether type.

23. The process as defined by claim 19, wherein said alcohol is a monoalcohol having from 1 to 4 carbon atoms.

24. The process as defined by claim 23, wherein said alcohol is a monoalcohol having from 1 to 3 carbon atoms.

25. The process as defined by claim 8, wherein an additional amount of quaternary onium chloride or bromide is added in said contacting step (1).

* * * * *